(12) United States Patent
Morimoto et al.

(10) Patent No.: US 6,320,652 B1
(45) Date of Patent: Nov. 20, 2001

(54) OPTICAL MEASURING APPARATUS

(75) Inventors: Teruo Morimoto, Osaka; Kazuhiko Naruse, Yahata; Makoto Kamiya, Sakai; Takashi Saika, Sennan, all of (JP)

(73) Assignee: Minolta Co., Ltd., Osaka (JP)

( * ) Notice: Subject to any disclaimer, the term of this patent is extended or adjusted under 35 U.S.C. 154(b) by 0 days.

(21) Appl. No.: 09/494,169

(22) Filed: Jan. 31, 2000

(30) Foreign Application Priority Data

Jan. 29, 1999 (JP) .................................................. 11-023096

(51) Int. Cl.⁷ .................................................... G01B 9/00
(52) U.S. Cl. ............................................................. 356/124
(58) Field of Search ................................. 356/124; 348/86, 348/79, 87, 88, 93, 125, 126, 129, 128, 131, 189, 92; 345/87; 382/141, 144

(56) References Cited

U.S. PATENT DOCUMENTS

| | | | |
|---|---|---|---|
| 5,293,178 | 3/1994 | Kobayashi | 345/87 |
| 5,696,550 | 12/1997 | Aoki et al. | 348/125 |
| 5,757,346 | * 5/1998 | Mita | 345/87 |

* cited by examiner

*Primary Examiner*—Frank G. Font
*Assistant Examiner*—Michael P. Stafira
(74) *Attorney, Agent, or Firm*—McDermott, Will & Emery

(57) ABSTRACT

An optical measuring apparatus used for measuring optical characteristics of a liquid crystal display panel (LCD panel) in a calibration thereof comprises a housing having a contacting portion directly contacting a surface of the LCD panel and disposed far from a region on the LCD panel to be measured. An optical system and a photosensor is provided in the housing with a predetermined positional relation, so that ambient illumination is shielded by the housing and stray rays emitted from the LCD panel and having exit angles larger than a predetermined maximum exit angle α are restricted by the optical system.

20 Claims, 15 Drawing Sheets

OPTICAL MEASURING APPARATUS

This application is based on patent application Hei.11-23096 filed in Japan, the contents of which are hereby incorporated by references.

BACKGROUND OF THE INVENTION

1. Field of the Invention

This invention relates to an optical measuring apparatus used, for example, in a calibration of an apparatus such as a liquid crystal display panel (hereinafter abbreviated as LCD panel).

2. Description of the Related Art

An optical measuring apparatus has conventionally been used in a manufacturing line of an LCD panel for measuring optical characteristics such as chromaticity and luminance. Adjustment of white balance, quality control and shipping inspection of the LCD panel are executed by using the result of the measurement of the optical characteristics.

A conventional optical measuring apparatus such as the LCD color analyzer CA-110 produced by MINOLTA CO., LTD. comprises a probe and a main unit. The probe includes a photosensor for receiving rays emitted from a region of an LCD panel which is to be measured (hereinafter abbreviated as measurement region). The main unit calculates xyY (chromaticity coordinates and luminance) and T∆uvY (correlated color temperature, color difference and luminance), which are established by Commission Internationale de l'Eclairage (CIE), by basing on output of the photosensor of the probe. The calculated values are displayed on a display panel of the main unit.

The above-mentioned conventional optical measuring apparatus for the LCD panel is a noncontact type apparatus, in which the probe is positioned distant by a predetermined distance from the LCD panel. It is necessary to position the probe accurately at the position distant from the predetermined distance from the LCD panel.

Furthermore, in the measurement using the noncontact type optical measuring apparatus, rays of ambient illumination are reflected by a surface of the LCD panel, so that the reflected rays can enter into the photosensor of the probe as stray rays. When the stray rays enter into the probe, that is, the reflected rays of the ambient illumination are included in rays directly emitted from the measurement region of the LCD panel, output value from the photosensor of the probe is varied. As a result, the optical characteristics of the LCD panel are not estimated accurately. Especially, when the luminance of the LCD panel is relatively low, the stray rays largely affects the accuracy of the measurement. For solving this problem, it is necessary to reduce the ambient illumination of the prove and the LCD panel.

In another conventional optical measuring apparatus such as the CRT color analyzer CA-100 produced by MINOLTA CO., LTD., which is used for measuring optical characteristics of a CRT (Cathode Ray Tube) apparatus, a probe is directly contacted on a measurement region on The CRT apparatus. When this contact type apparatus is used for measuring the optical characteristics of the LCD panel, it causes the following problems.

The LCD panel is configured by that a liquid crystal layer is disposed between two glass plates for making the thickness of the liquid crystal layer even. When the probe is directly contacted on the surface of the LCD panel, the glass plate to which the probe is contacted is warped, so that the thickness of the liquid crystal layer in a region around the contacting portion of the probe and the LCD panel is varied. When the thickness of the liquid crystal layer is varied, colors of an image displayed on the region of the LCD panel is varied. In this case, the region where the thickness of the liquid crystal layer is varied corresponds to the measurement region. Thus, it is substantially impossible to measure the optical characteristics of the LCD panel by the conventional contact type apparatus.

On the other hand, it is conventionally known that the chromaticity and the luminance of the image displayed on the LCD panel varies when an observer moves from the front center of the LCD panel to the side thereof. This phenomenon is caused by light distribution of the LCD panel, that is, the larger the exit angle of the rays emitted from the LCD panel becomes, the smaller the intensity of the light becomes.

A light distribution of a typical LCD panel on the market is shown in FIG. 19A. The light distribution of the LCD panel is substantially symmetrical with respect to the normal "N" at the center of the LCD panel 12 in both of the vertical direction XX and the horizontal direction YY, so that an image can be displayed preferably when it is observed from the front center thereof. However, when the LCD panel is observed from the side at an observing angle larger than a predetermined angle α against the normal "N", the chromaticity and the luminance of the image are largely varied. It is generally said that the angle of view of the LCD panel is narrow.

In the conventional noncontact type optical measuring apparatus, the probe is positioned distant from the LCD panel, so that the probe receives not only paraxial rays but also the rays having exit angles larger than the predetermined angle α (in the following description, the angle α is called "maximum exit angle"). Thus, the accuracy and the repeatability of the measurement of the optical characteristics of the LCD panel by the conventional optical measuring apparatus are not so high.

Furthermore, in a kind of the LCD panel, the symmetry of the light distribution against the normal "N" will be deteriorated as shown in FIG. 19B when the display of the image is changed. For example, when the color of the image is gradually changed from white to black, it is observed that an exit angle of rays against the normal "N", at which the luminance of the image becomes the largest, increases. The variation of the light distribution of the LCD panel on the market is generally restricted only in the vertical direction XX in the figure. In this description, the spatial oblique coordinates are designated by symbols XX, YY and ZZ for distinguishing from tristimulus values X, Y and Z.

As shown in FIG. 20, even when the photosensor R of the probe is disposed on the normal "N" at the center of the LCD panel 12 for receiving rays emitted from the measurement region 121, the output $S_R$ from the photosensor R varies corresponding to the variation of the light distribution of the LCD panel 12.

SUMMERY OF THE INVENTION

A purpose of this invention is to provide a contact type optical measuring apparatus by which optical characteristics of an object such as an LCD panel can be measured accurately.

An optical measuring apparatus in accordance with an aspect of the present invention comprises a housing with a contact portion for contacting on a surface of an object at position distant from a region to be measured, and a photosensor fixed on the housing and positioned with respect to the contact portion.

By such a configuration, when the optical measuring apparatus is directly contacted on the object such as the LCD panel, thickness of a liquid crystal layer in the vicinity of the contact portion varies. However, the contact portion is distant from the region to be measured (measurement region), so that the thickness of the liquid crystal layer in the measurement region is hardly varied. Since the photosensor is fixed on the housing, the photosensor is automatically positioned at the position distant by a predetermined distance from the surface of the LCD panel. Furthermore, the housing shields the ambient illumination, so that no stray ray enters into the photosensor.

Furthermore, it is preferable further to comprise an optical system guiding rays emitted from the region to be measured and having exit angles equal to or smaller than a predetermined angle. By such a configuration, stray rays having the exit angle larger than the predetermined angle hardly enter the photosensor. The noise component due to the stray rays becomes much smaller, so that the S/N of the output signal of the apparatus increases.

DETAILED DESCRIPTION OF THE EMBODIMENT

An embodiment of an optical measuring apparatus in accordance with this invention is described.

Figure 1:
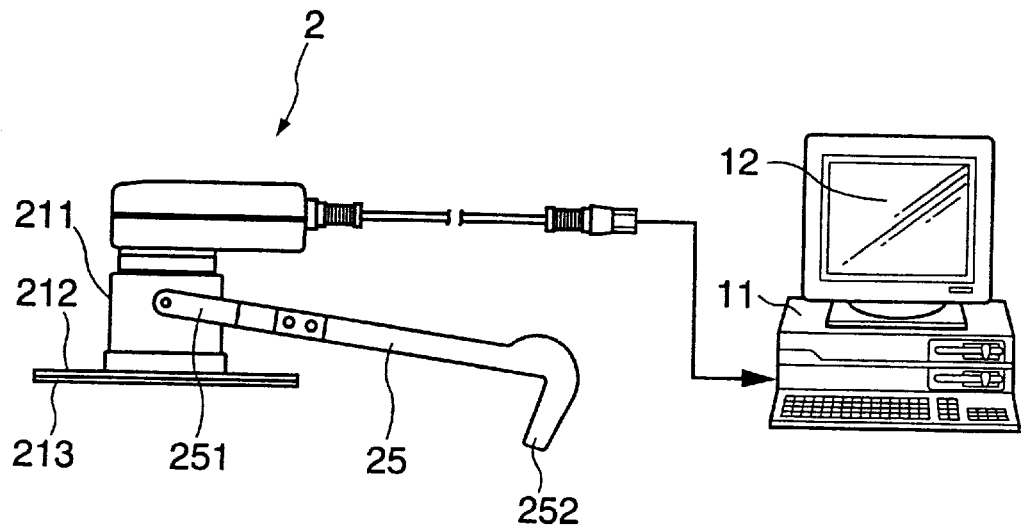
FIG. 1 is a front view showing a calibration system of LCD panel using an optical measuring apparatus in accordance with the present invention.

A calibration system of an LCD panel using the optical measuring apparatus in the embodiment is shown in FIG. 1. In the calibration system, an LCD panel 12 is electrically connected to a (personal) computer 11. Chromaticity, that is, tristimulus values of the LCD panel 12 is measured by an optical measuring apparatus 2, and result of measurement is inputted to the computer 11 through an interface such as RS232C and USB (Universal Serial Bus). The result of measurement is processed by a compensation program previously installed in the computer 11 for adjusting white balance of the LCD panel 12. As mentioned above, the light distribution of the LCD panel in the market generally varies from the symmetry in the vertical direction XX, but it is substantially symmetrical in the horizontal direction YY. Thus, it is assumed that the light distribution characteristics in the vertical direction and in the horizontal direction of the LCD panel described below follow these preconditions.

Figure 2:
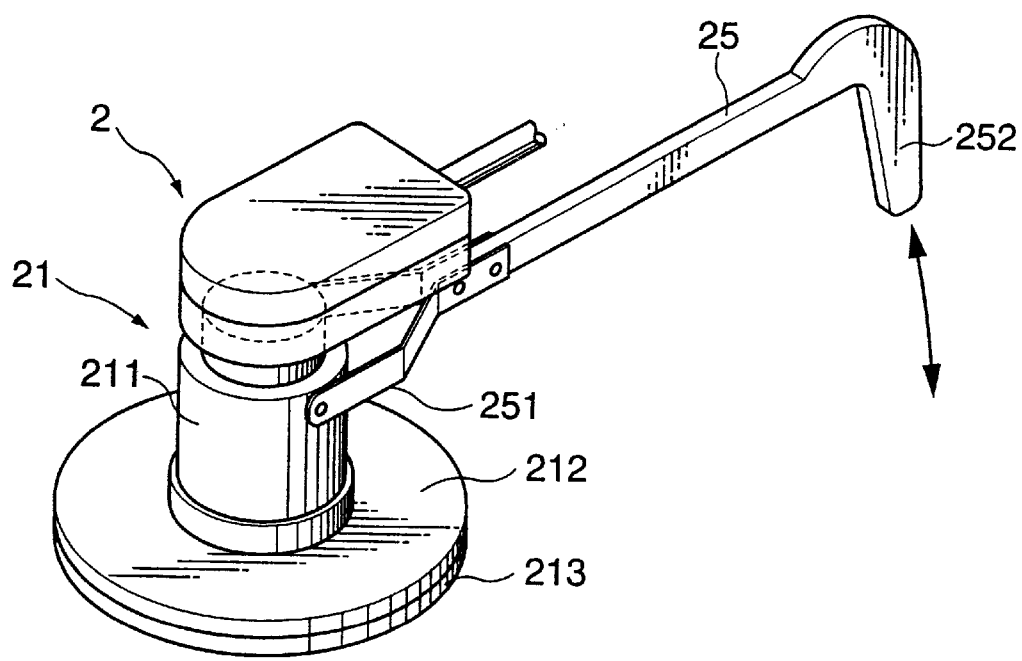
FIG. 2 is a perspective view showing an appearance of the optical measuring apparatus in an embodiment.
Figure 3:
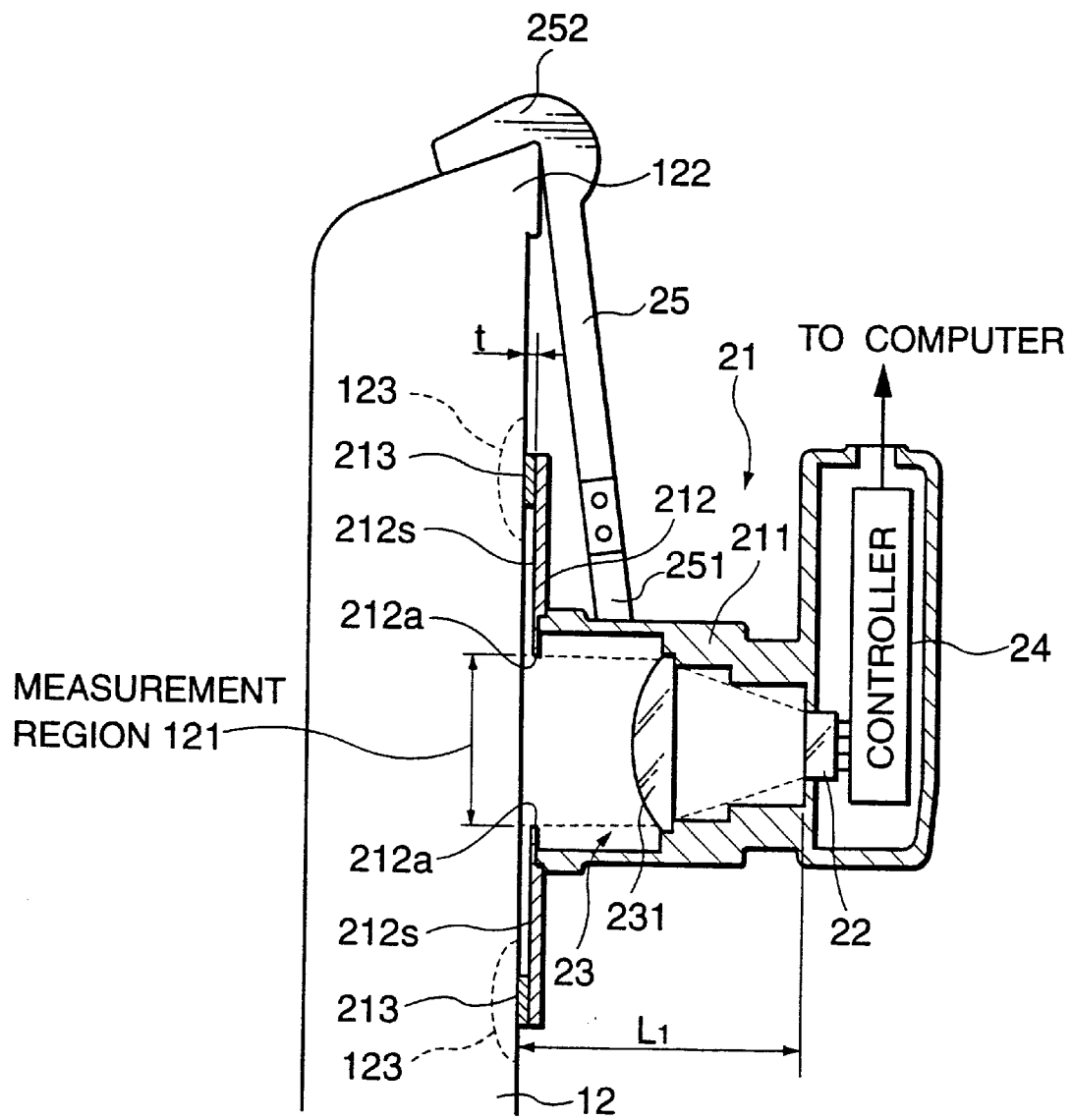
FIG. 3 is a cross-sectional front view showing a configuration of the optical measuring apparatus in the embodiment when it is hanged on the LCD panel.

An appearance of the optical measuring apparatus in this embodiment is shown in FIG. 2, and a cross-sectional configuration thereof is shown in FIG. 3. In FIG. 3, the optical measuring apparatus 2 is hanged on the LCD panel 12.

As can be seen from the figures, a photosensor 22, an optical system 23, a controller 24 are provided in a housing 21 of the optical measuring apparatus 2. The photosensor 22 receives rays emitted from a measurement region 121 on the LCD panel 12. The optical system 23 guides the rays from the measurement region 121 to the photosensor 22. The controller 24 calculates tristimulus values X, Y and Z by using the output signals from the photosensor 22, and outputs the signals corresponding to the tristimulus values X, Y and Z to the computer 11. The tristimulus values X, Y and Z show the chromaticity and the luminance of an image displayed on the measurement region 121 of the LCD panel 12. Furthermore, a hook 25 by which the optical measuring apparatus 2 is hanged on the LCD panel 12 is provided outside the housing 21.

The housing 21 is configured by a tubular portion 211 made of, for example, ABS (acrylonitrile-butadiene-styrene copolymer) resin and a ring shaped flange 212 fixed at an open end (left side in FIG. 3) of the tubular portion 211 and made of, for example, polycarbonate. Furthermore, a ring sheet 213, for example, made of rubber is fixed on a surface 212s of the flange 212 along the outer periphery thereof. The ring sheet 213 is to be contacted on the surface of the LCD panel 12.

When the ring sheet 213 is contacted to the surface of the LCD panel 12 shown in FIG. 3, the flange 212 is positioned distant by a thickness "t" of the ring sheet 213 from the surface of the LCD panel 12. The photosensor 22 and the optical system 23 are respectively disposed at predetermined positions with respect to the surface 212s of the flange 212 in the housing 21 with predetermined accuracy, so that the photosensor 22 and the optical system 23 are precisely positioned with respect to the surface of the LCD panel 12.

That is, the optical measuring apparatus 2 in this embodiment is a contact type one, in which the ring sheet 213 contacting on the surface of the LCD panel 12 serves as a contacting portion for positioning the photosensor 22 at a position distant by a predetermined length "$L_1$" from the measurement region 121 on the LCD paned 12.

In this embodiment, since the hook 25 is used for fixing the optical measuring apparatus 2 on the surface of the LCD panel 12, a rear end 251 of the hook 25 having substantially Y-letter section is rotatably pivoted on an outer cylindrical surface of the tubular portion 211 of the housing 21 and a top end 252 of the hook 25 is engaged with an upper surface 122 of the LCD panel 12.

However, the method for fixing the optical measuring apparatus 2 on the surface of the LCD panel 12 is not restricted by this configuration using the hook 25. It is possible to use a clip, a stand, a fastener, and so on. Alternatively, in case of disposing the LCD panel 12 in a manner so that the surface thereof looks upwards, no means for fixing the optical measuring apparatus 2 on the surface of the LCD panel 12 is necessary. When the housing 21 of the optical measuring apparatus 2 is disposed on the surface of the LCD pane 12, the photosensor 22 on the optical measuring apparatus 2 is positioned at a position distant by the predetermined distance "$L_1$" from the surface of the LCD panel 12.

Furthermore, it is possible to handle the optical measuring apparatus 2 for contacting on the surface of the LCD panel 12 by an operator without using the fixing means. Still furthermore, it is possible to use a robot automatically for contacting the optical measuring apparatus 2 on the surface of the LCD panel 12.

Figure 4:
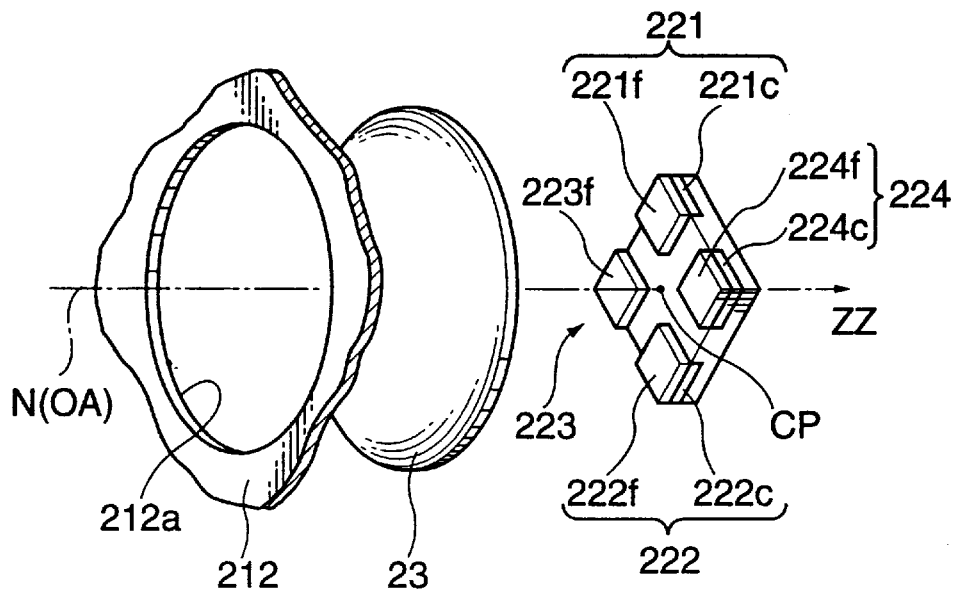
FIG. 4 is a perspective view showing a configuration and positional relations of a flange, an optical system and a photosensor of the optical measuring apparatus in the embodiment.

Positional relations of the flange 212, a lens 231 of the optical system 23 and the photosensor 22 in the housing 21 is shown in FIG. 4. Furthermore, a front view of the photosensor 22 is shown in FIG. 5.

As can be seen from FIGS. 3 and 4, a circular opening 212a is formed at the center of the flange 212. In the measurement shown in FIG. 3, the opening 212a faces the measurement region 121 on the LCD panel 12 closely, so that only the rays emitted from the measurement region 121 can reach to the photosensor 22 via the optical system 23. By such a configuration, the opening 212a of the flange 212 serves as an aperture stop of the optical system 23.

The optical system 23 is configured to guide only the rays having exit angles equal to or smaller than a predetermined maximum exit angle α such as 10 degrees among all the exit rays from the measurement region 121 to the photosensor 22. By such a configuration, an accurate measurement, in which the affect of the light distribution of the LCD panel 12 is restricted, can be realized. Detailed configuration of the optical system 23 for restricting the rays having the exit angle larger than the predetermined maximum angle α will be described below.

Figure 5:
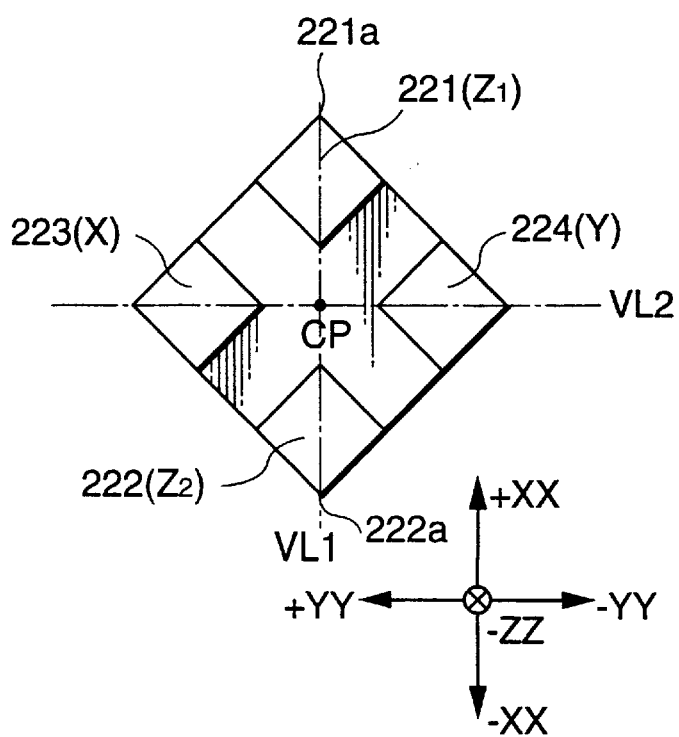
FIG. 5 is a front view showing a configuration of the photosensor in the embodiment.

As can be seen from FIGS. 4 and 5, the photosensor 22 has a first to a fourth photosensitive portions 221 to 224. The first photosensitive portion 221 and the second photosensitive portion 222 have substantially the same spectral sensitivity characteristics of the spectral sensitivity $\bar{z}(\lambda)$ among three spectral sensitivities $\bar{x}(\lambda)$, $\bar{y}(\lambda)$ and $\bar{z}(\lambda)$. These three spectral sensitivities $\bar{x}(\lambda)$, $\bar{y}(\lambda)$ and $\bar{z}(\lambda)$ are defined as spectral sensitivities of a standard human observer by the CIE. The spectral sensitivity $\bar{z}(\lambda)$ has the highest sensitivity in a region of wavelength of blue. The third photosensitive portion 223 has the spectral sensitivity of $\bar{x}(\lambda)$ having has the highest sensitivity in a region of wavelength of red. The fourth photosensitive portion 224 has the spectral sensitivity of $\bar{y}(\lambda)$ having has the highest sensitivity in a region of wavelength of green.

The first photosensitive portion 221 and the second photosensitive portion 222 are disposed symmetrical with respect to the center CP of the photosensor 22, and photosensitive surfaces of them are on the same plane. The third photosensitive portion 223 and the fourth photosensitive portion 224 are also disposed symmetrical with respect to the center CP of the photosensor 22 but a line VL2 binding the third photosensitive portion 223 and the fourth photosensitive portion 224 crosses at right angle with a line VL1 binding the first photosensitive portion 221 and the second photosensitive portion 222.

As shown in FIG. 4, four photosensitive layers 221c, 222c and 224c (the layer corresponding to the photosensitive portion 223 is not illustrated) are formed in the vicinity of four corners on a principal plane of a substrate. Blue filters 221f and 222f, which passes the light having wavelength in a region of blue in large quantities, are fixed on the photosensitive layers 221c and 222c. Thus, the first and second photosensitive portions 221 and 222 having the spectral sensitivity $\bar{z}(\lambda)$ are formed. Similarly, a red filter 223f, which passes the light having wavelength in a region of red in large quantities, is fixed on the photosensitive layers not shown in the figure. A green filter 224f, which passes the light having wavelength in a region of green in large quantities, is fixed on the photosensitive layers 224c. Thus, the third and fourth photosensitive portions 223 and 224 respectively having the spectral sensitivity $\bar{x}(\lambda)$ and $\bar{y}(\lambda)$ are formed.

The photosensor 22 is fixed on the housing 21 in a manner so that the photosensitive surfaces of the first to fourth photosensitive portions 221 to 224 are distant by the distance "$L_1$" from the surface of the LCD panel 12 or the surface of the ring sheet 213, and the center CP of the photosensor 22 coincides with the normal "N" of the measurement region 121 on the LCD panel 12 when the housing 21 is hanged on the surface of the LCD panel 12. Furthermore, the line VL1 coincides with the vertical direction XX and the line VL2 coincides with the horizontal direction YY. By such a configuration, the first photosensitive portion 221 is positioned in a region of +XX, and the second photosensitive portion 222 is positioned in a region −XX.

Figure 19A:
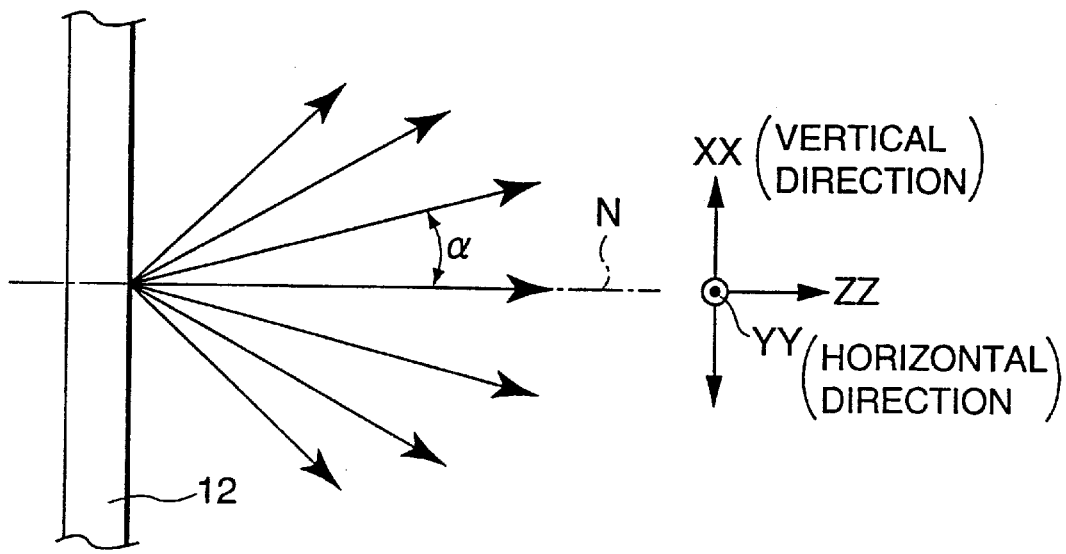
FIG. 19A is a side view showing the typical light distribution of the LCD panel on the market.
Figure 19B:
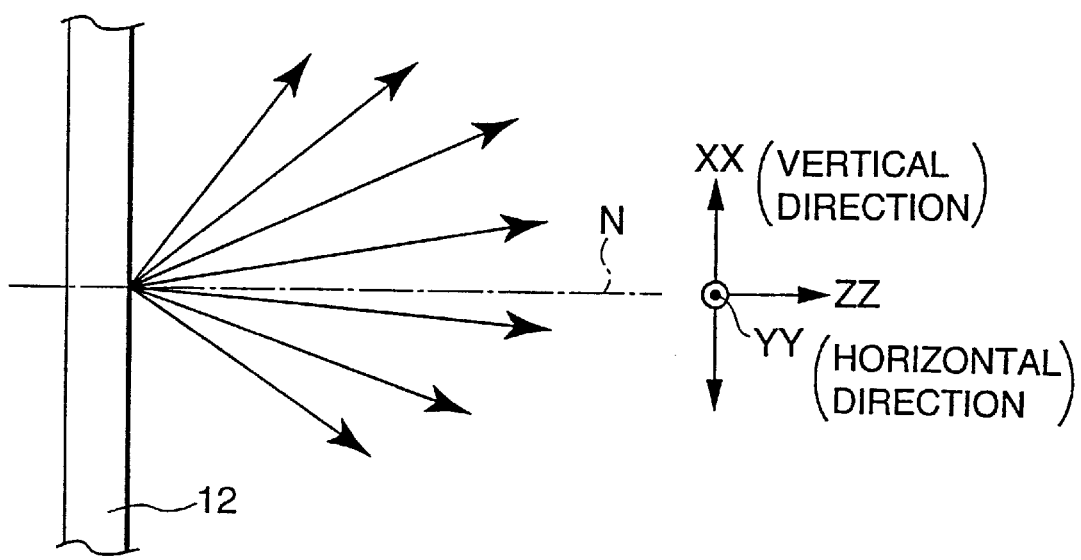
FIG. 19B is a side view showing the variation of the light distribution of the LCD panel.
Figure 20:
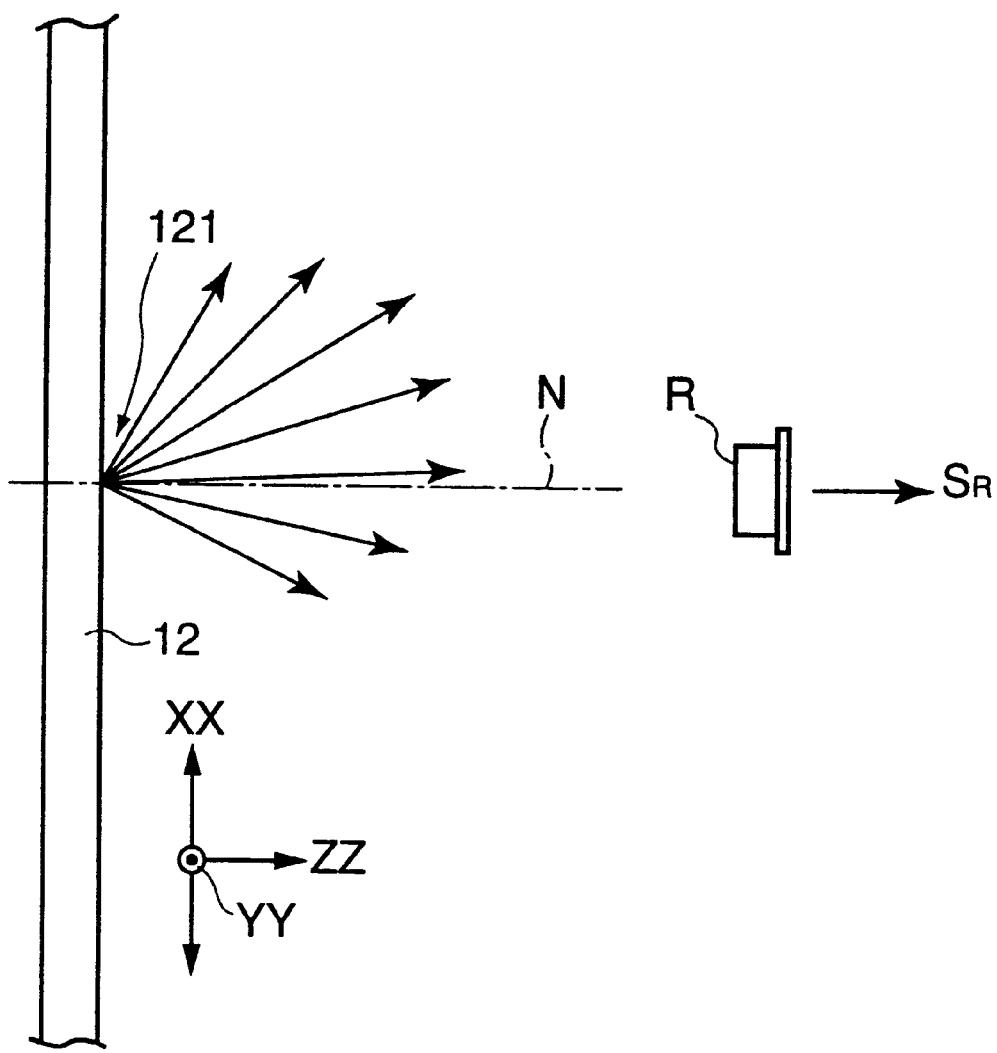
FIG. 20 is a side view for explaining the problem of the conventional noncontact type optical measuring apparatus.

The reason why the above-mentioned configuration is taken is described. It is considered an assumption that only one photosensitive portion having the spectral sensitivity $\bar{z}(\lambda)$ is provided on the center of the photosensor 22, that is, three photosensitive portions are positioned on the horizontal line VL2 in FIG. 5. When the light distribution of the LCD panel 12 in the vertical direction XX is varied from FIG. 19A to FIG. 19B, level of an output signal from the photosensitive portion varies. Thus, it is difficult to measure the optical characteristics of the LCD panel accurately. To the contrary, two photosensitive portions 221 and 222 are disposed on the vertical line VL1 and symmetrical with respect to the center CP in the embodiment. The output signals of the photosensitive portions 221 and 222 are added as the output signal showing the spectral sensitivity $\bar{z}(\lambda)$. Thus, even when the light distribution of the LCD panel 12 is varied, the variation of the output signal of the spectral sensitivity $\bar{z}(\lambda)$ becomes very small.

Instead of adding the output signals of the photosensitive portions 221 and 222, it is possible to use a mean value or weighted value of the output signals of the photosensitive portions 221 and 222 is used as the output signal showing the spectral sensitivity $\bar{z}(\lambda)$.

In this embodiment, two photosensitive portions 221 and 222 are provided for measuring the tristimulus value Z. However, it is possible to provide more than three photosensitive portions for measuring the tristimulus value Z. Hereupon, since the value of the tristimulus value Z is the smallest in the tristimulus values X, Y and Z of the LCD panel supplied in the market, a plurality of photosensitive portions are provided for measuring the tristimulus value Z. By such a configuration, the level of the output signal showing the tristimulus value Z can be increased, so that the optical characteristics of the LCD panel 12 can be measured accurately. In summary, a sample image such as white image is displayed on the measurement region 121 of the LCD panel 12, the smallest the output signal among the tristimulus values X, Y and Z is increased by any method such as adding two output signals from independent two photosensitive portions.

In this embodiment, the first to fourth photosensitive portions 221 to 224 having substantially the same spectral sensitivities as those of the human spectral sensitivities are provided in the photosensor 22, so that the color of the image displayed on the measurement region 121 on the LCD panel 12 can be measured as the tristimulus values X, Y and Z (Z1 and Z2). Four analogue signals SX, SY, SZ1 and SZ2 corresponding to the tristimulus values X, Y, Z1 and Z2 are outputted to the controller 24. After compensation by the controller 24, digital signals corresponding to the compensated tristimulus values X, Y and Z are outputted from the optical measuring apparatus 2.

The configuration of the photosensor 22, however, is not restricted by the above-mentioned configuration. It is possible to provide another photosensitive portion having the spectral sensitivity of $\bar{z}(\lambda)$ on the line VL2 instead of the first and second photosensitive portions 221 and 222. By this configuration, the tristimulus values X, Y and Z can be measured. In this case, it is preferable that sensitivity of the photosensitive region or transparency of the blue filter for the tristimulus value Z is higher than that of the others.

Figure 6:
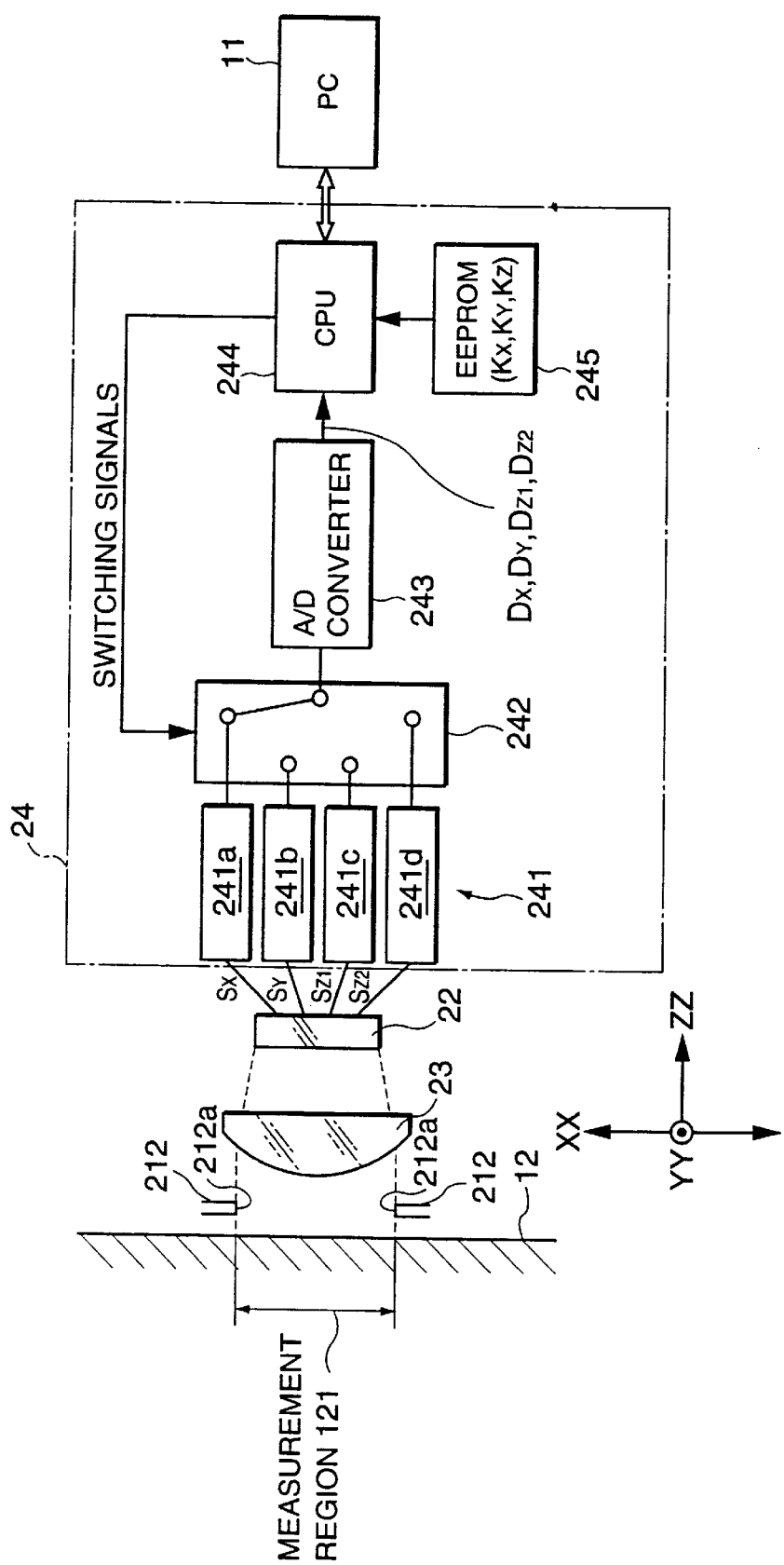
FIG. 6 is a block diagram showing a configuration of a control circuit of the optical measuring apparatus in the embodiment.

A block diagram of the controller 24 of the optical measuring apparatus 2 is shown in FIG. 6. The controller 24 comprises an amplifying circuit 241 consisting of four amplifiers 241a to 241d. The amplifiers 241a to 241d are respectively connected to the photosensitive portions 221 to 224 of the photosensor 22, so that the analogue signals SX, SY, SZ1 and SZ2 outputted from the photosensitive portions 221 to 224 are amplified. The amplified analogue signals corresponding to the signals SX, SY, SZ1 and SZ2 from the amplifiers 241a to 241d are inputted to corresponding terminals of a multiplexer 242.

The multiplexer 242 serially switches the connection between one of the amplifiers 241a to 241d and an A/D converter 243 responding to switching signals from a CPU (Central Processing Unit) 244. The amplified analogue signals corresponding to the signals SX, SY, SZ1 and SZ2 are serially inputted to the A/D converter 243 and converted to digital signals DX, DY, DZ1 and DZ2 by the A/D converter 243. When the CPU 244 receives the converted digital signals DX, DY, DZ1 and DZ2 from the A/D converter 243, the CPU 244 calculates actual tristimulus values X, Y and Z from the digital signals DX, DY, DZ1 and DZ2 and compensation factors KX, KY and KZ which are previously memorized in an EEPROM (Electrically Erasable Programmable Read Only Memory) 245. The calculated tristimulus values X, Y and Z are outputted to the computer 11.

Figure 7:
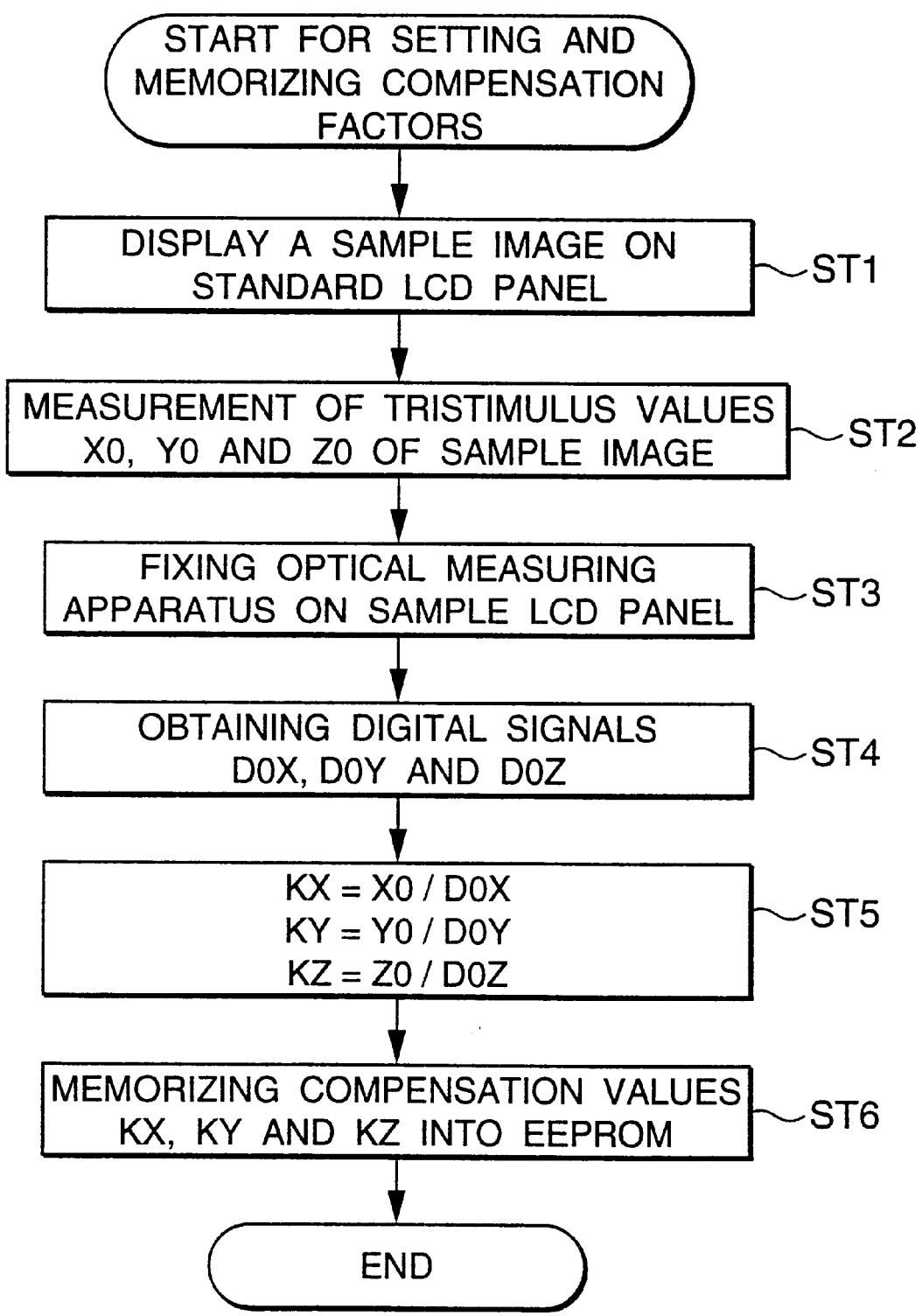
FIG. 7 is a flowchart for explaining a process for memorizing compensation values into an EEPROM prior to the calibration in the calibration system.
Figure 8:
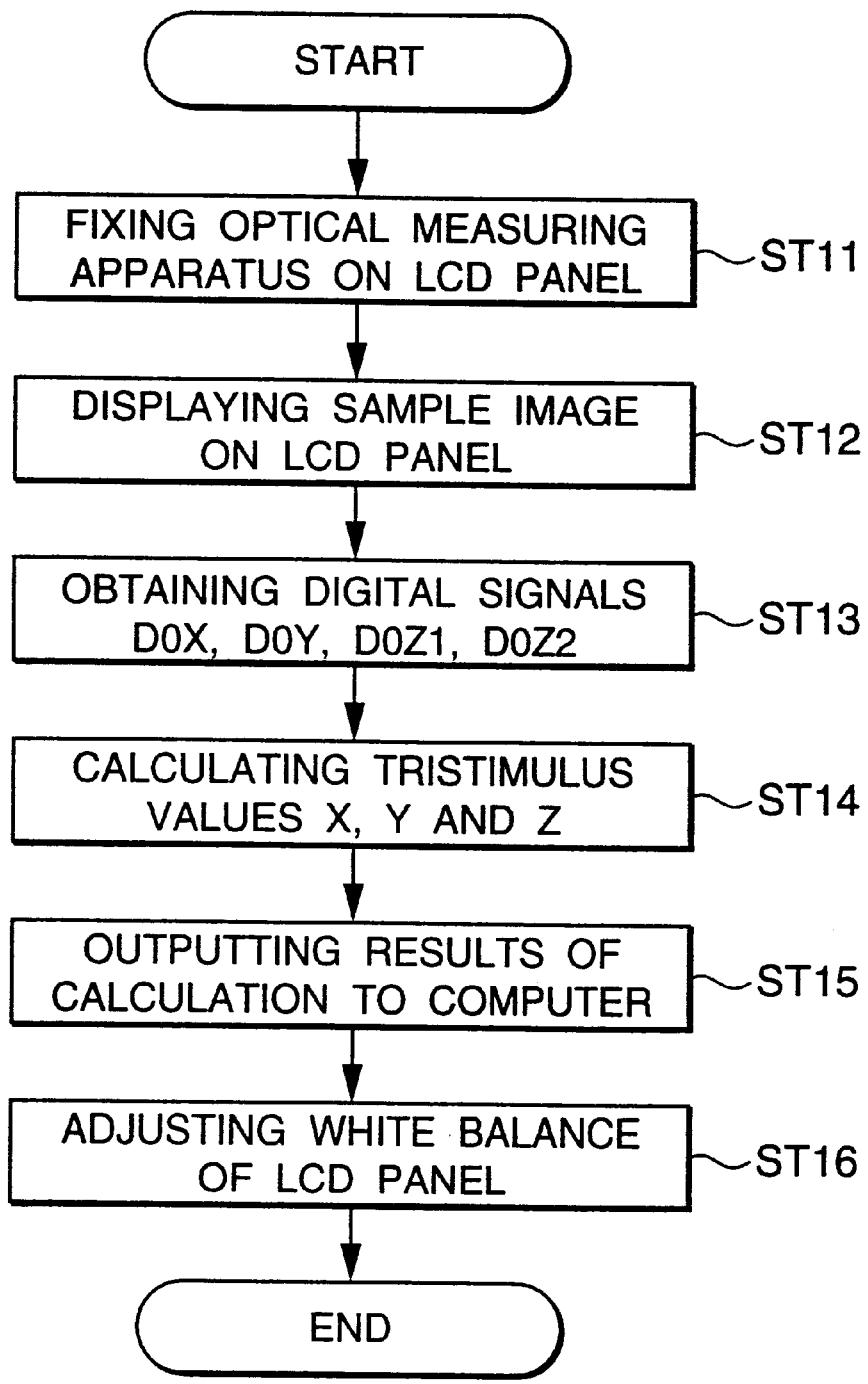
FIG. 8 is a flowchart for explaining a process of the calibration in the calibration system.

An example of the calibration process of the LCD panel 12 using the optical measuring apparatus 2 in this embodiment is described with reference to FIGS. 7 and 8. FIG. 7 shows a flow for memorizing the compensation factors KX, KY and KZ into the EEPROM 245 prior to the calibration process. FIG. 8 shows a flow of the calibration process.

At first, the process for memorizing the compensation factors KX, KY and KZ is described with reference to FIG. 7. A sample LCD panel which will be the standard is prepared, and a sample image such as a white image to be measured is displayed on the sample LCD panel (step ST1). Subsequently, the tristimulus values X0, Y0 and Z0 of the sample image displayed on the sample LCD panel are measured by a conventional measuring apparatus such as the spectral radiance meter CS-1000 produced by MINOLTA CO., LTD. (step ST2).

After that, the optical measuring apparatus 2 is contacted on the sample LCD panel by hanging the top end 252 of the hook 25 of the optical measuring apparatus 25 on the upper surface of the sample LCD panel (step ST3). The CPU 244 outputs the switching signals to the multiplexer 242 for serially switching the connection of the amplifiers 241a to 241d and the A/D converter 243. Therefore, the CPU 244 obtains digital signals D0X, D0Y, D0Z1 and D0Z2 outputted from the A/D converter 243. Furthermore, the CPU 244 calculates a digital signal D0Z by adding the digital signals D0Z1 and D0Z2 (step ST4).

Subsequently, the CPU 244 calculates the compensation factors KX, KY and KZ by the following equations (step ST5), and memorizes the calculated compensation factors KX, KY and KZ into the EEPROM 245 (step ST6).

$$KX=X0/D0X$$

$$KY=Y0/D0Y$$

$$KZ=Z0/D0Z$$

In this embodiment, the tristimulus values X0, Y0 and Z0 are inputted by operation of a keyboard (not shown in the figure) by an operator and temporarily stored into a RAM (Random Access Memory: not shown in the figure) of the optical measuring apparatus 2. The digital signals D0X, D0Y, D0Z1 and D0Z2 outputted from the A/D converter 243 are temporarily stored in the RAM and the signals D0Z1 and D0Z2 are read out from the RAM and the digital signal D0Z is calculated by adding the signals D0Z1 and D0Z2. Subsequently, the CPU 244 reads out the tristimulus values X0, Y0 and Z0 from the RAM, and it calculates the compensation factors KX, KY and KZ by following the above-mentioned equations. The compensation factors KX, KY and KZ are automatically memorized in the EEPROM 245. However, it is possible manually to calculate the values of the digital signal D0Z and the compensation factors KX, KY and KZ and they are inputted to the EEPROM 245 by the keyboard operation of the operator.

Next, the calibration process of the LCD panel using the optical measuring apparatus 2 is described with reference to FIG. 8. As mentioned above, the compensation factors KX, KY and KZ are previously memorized in the EEPROM 245 of the controller 24 in the optical measuring apparatus 2.

The optical measuring apparatus 2 is contacted on the LCD panel 12 by hanging the top end 252 of the hook 25 of the optical measuring apparatus 25 on the upper surface 122 of the LCD panel 12 (step ST11). The same sample image as displayed on the sample LCD panel is displayed on the measurement region 121 on the LCD panel 12 by the computer 11 (step ST12).

When the sample image is displayed on the measurement region 121 on the LCD panel 12, the photosensitive layer 221 to 224 of the photosensor 22 of the optical measuring apparatus 2 output four analogue signals SX, SY, SZ1 and SZ2 corresponding to the tristimulus values X, Y and Z (Z1 and Z2). Hereupon, the CPU 244 controls the multiplexer 242 to switching the connection of the amplifiers 241a to 241d and the A/D converter 243 for obtaining the digital signals D0X, D0Y, D0Z1 and D0Z2 outputted from the A/D converter 243. The obtained digital signals D0X, D0Y, D0Z1 and D0Z2 are temporarily stored in the RAM (not shown in the figure) (step ST13).

Subsequently, the CPU 244 reads out the compensation factors KX, KY and KZ from the EEPROM 245, and calculates the actual tristimulus values X, Y and Z of the sample image displayed on the measurement region 121 on the LCD panel 12 (step ST14). That is, the CPU 244 calculates a digital signal D0Z by adding the digital signals D0Z1 and D0Z2. After that, the CPU 244 calculates the actual tristimulus values X, Y and Z by the following equations.

$$X = KX \cdot D0X$$
$$Y = KY \cdot D0Y$$
$$Z = KZ \cdot D0Z$$

In this embodiment, the analogue signals SZ1 and SZ2 outputted from the first and second photosensitive portions 221 and 222 are respectively amplified by the different amplifiers 241c and 241d. However, it is possible to amplify the analogue signals SZ1 and SZ2 from the first and second photosensitive portions 221 and 222 by the same amplifier. In the latter case, the amplifier outputs a signal corresponding to the addition of the amplified signals of the SZ1 and SZ2, so that the above-mentioned adding process of the D0Z1 and D0Z2 can be omitted.

When the actual tristimulus values X, Y and Z are calculated, the CPU 244 outputs the result of the calculation, that is, the actual tristimulus values X, Y and Z to the computer 11 via an interface such as RS232C and USB (step ST15). When the computer receives the result of the calculation, it executes the adjustment of the white balance of the LCD panel 12 by a program of the calibration of the LCD panel 12 which is previously installed in the computer 11 (step ST16).

In the above-mentioned calibration system using the optical measuring apparatus of this embodiment, the tristimulus values X, Y and Z are measured as optical characteristics of the LCD panel 12. However, the optical measuring apparatus in accordance with the present invention is not restricted by measure the tristimulus values X, Y and Z. It is possible to measure and output other optical characteristics such as chromaticity and luminance by the optical measuring apparatus.

As mentioned above, the optical measuring apparatus of the embodiment has three characteristic configurations. First, the optical measuring apparatus 2 is a contact type one which is directly contacted on the surface of the LCD panel 12 for measuring the optical characteristics of the measurement region 121. Second, the optical system 23 introduces only the rays having the exit angle equal to or smaller than the angle α and emitted from the measurement region 121 to the photosensitive portions 221 to 224 of the photosensor 22. Third, two photosensitive portions 221 and 222 having the same spectral sensitivity corresponding to the tristimulus value Z are formed on the photosensor 22 with regard to the variation of the light distribution in the vertical direction XX. Effects of these three characteristic configurations will be considered.

As shown in FIG. 3, when the optical measuring apparatus 2 is hanged on the LCD panel 12, the ring sheet 213 contacts on the surface of the LCD panel 12. A glass panel constituting the LCD panel 12 is warped by a component pushing the surface of the LCD panel 12 due to the weight of the optical measuring apparatus 2, so that a thickness of a liquid crystal layer of the LCD panel 12 in a ring shaped region 123 shown by dotted line in FIG. 3, which is formed around the contacting portion of the ring sheet 213 and the surface of the LCD panel 12, is varied. As a result, the color of the image displayed in the circular region 123 is varied. Hereinafter, the region 123 is called color varied region.

As can be seen from FIG. 3, the inner diameter of the ring sheet 213 is much larger than the diameter of the opening 212a of the flange 212, so that the color varied region 123 is disposed far from the measurement region 121. The rays emitted from the color varied region 123 are shielded by the flange 212 and may not enter into the photosensor 22. Under such the condition, the tristimulus values X, Y and Z showing the chromaticity and the luminance of the image displayed on the measurement region 121 are measured. Thus, even when a part of the optical measuring apparatus 2 contacts on the surface of the LCD panel 12, the chromaticity and the luminance of the image displayed on the measurement region 121 can be measured precisely without receiving any affect from the color varied region 123.

Furthermore, the photosensor 22 is relatively positioned with respect to the flange 212 or the ring sheet 213, so that the distance between the photosensor 22 and the surface of the LCD panel 12 is automatically fixed by the distance "$L_1$". Thus, the chromaticity and the luminance of the image displayed on the measurement region 121 can be measured with high accuracy and high repeatability.

Still furthermore, most of the ambient illumination is shielded by the tubular portion 211 and the flange 212 of the housing 21, so that the accuracy of the measurement hardly reduced due to the stray rays. The ring sheet 213 encloses the measurement region 121 completely, so that it shields the rays of the ambient illumination so as not to enter into the measurement region 121. Since the tubular portion 211 and the flange 212 of the housing 21 are respectively made of resin materials, it is necessary to fill a pigment with light absorptivity into the resin materials. Alternatively, it is necessary to spread a paint with light absorptivity on inner and/or outer surfaces of the tubular portion 211 and the flange 212. Furthermore, it is possible to form the tubular portion 211 and the flange 212 by an opaque material such as metal and ceramics with regard to shield the ambient illumination.

In the above-mentioned embodiment, the ring sheet 213 is fixed on the flange 212 along the outer periphery thereof. However, it is possible to fix a plurality of strips of thin sheet on the flange 212, partially. The material of the ring sheet 213 or the strips is not restricted by the rubber. Another material with a predetermined thickness and softness so as not to injure the surface of the LCD panel 12 can be used.

Figure 9:
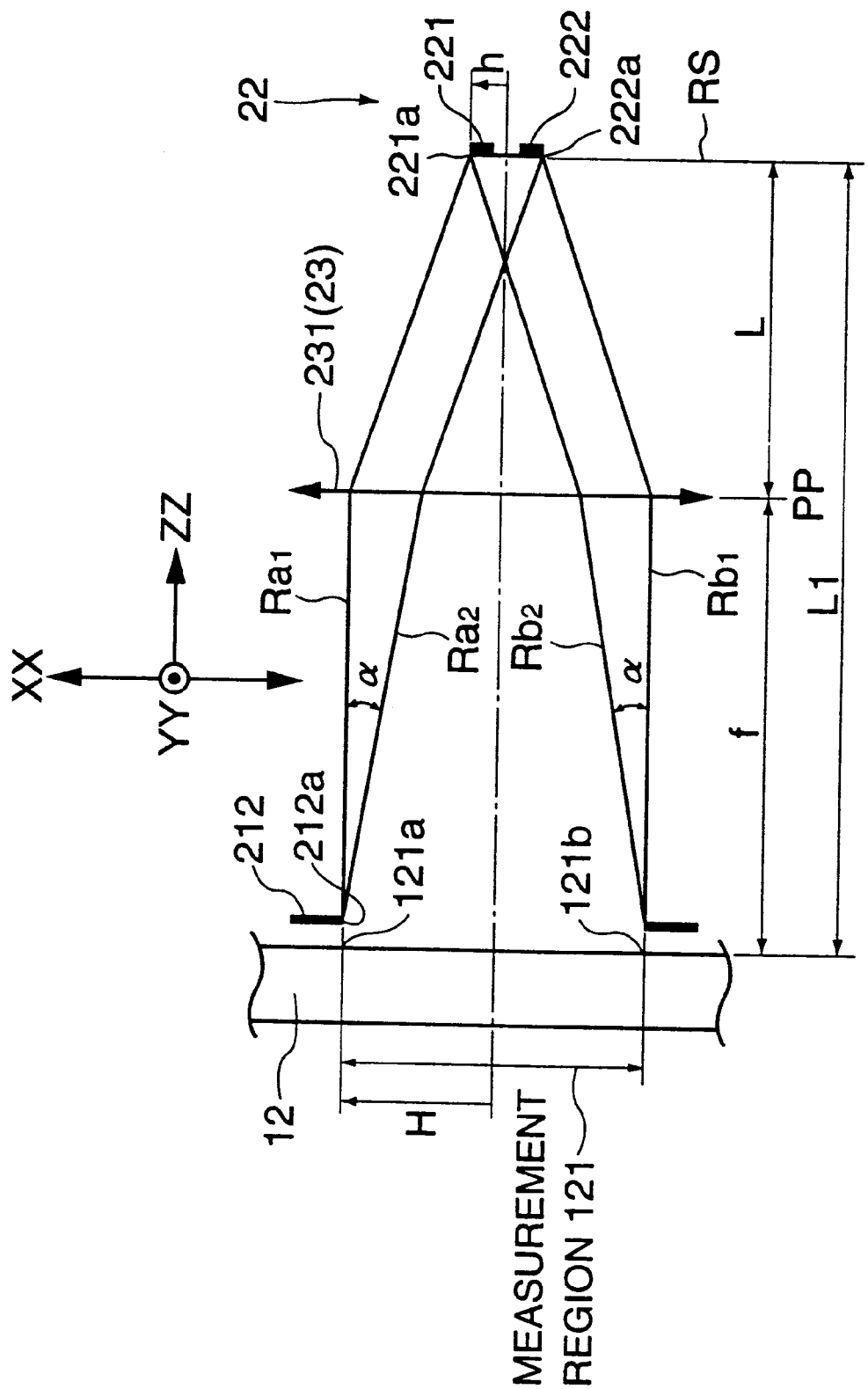
FIG. 9 is an optical path chart of the optical system in the embodiment.

Positional relations of the flange 212, the optical system 23 and the photosensor 22 are shown in FIG. 9. The optical system 23 includes, for example, a single plano-convex lens 231 having a positive power. The plano-convex lens 231 is disposed in a manner so that the convex face of the lens 231 faces the measurement region 121 and satisfies the following two equations.

$$f = |2 \cdot h / \tan \alpha|$$
$$L = (H - h) \cdot f / H$$

Hereupon, the symbol "f" designates a focal length of the lens 231; the symbol "h" designates the maximum height of the photosensitive portion 221 to 224 of the photosensor 22 from the optical axis of the lens 231 on the photosensing plane RS; the symbol "L" designates a distance from a principal point PP of the lens 231 in the image side to the photosensing plane RS; and the symbol "H" designates the maximum height of the measurement region 121 from the optical axis of the lens 231.

By such a configuration, only the rays having the exit angle equal to or smaller than the exit angle α and emitted from the measurement region 121 can reach to the photosensing plane RS of the photosensor 22.

When it is assumed that the lens 231 has no aberration at all or the aberration of the lens 231 is very small, a ray $R_{a1}$ emitted in the normal direction ZZ from an upper end 121a of the measurement region 121 crosses a ray $R_{b2}$ emitted with the maximum exit angle α from a lower end 121b of the measurement region 121 at a point 221a which is the top end of the first photosensitive portion 221. Similarly, a ray $R_{b1}$ emitted in the normal direction ZZ from the lower end 121b of the measurement region 121 crosses a ray $R_{a2}$ emitted with the maximum exit angle α from the upper end 121a of the measurement region 121 at a point 222a which is the bottom end of the second photosensitive portion 222. The same relations are conformed in the horizontal direction YY. Thus the first to fourth photosensitive portions 221 to 224 receive only the rays emitted from the measurement region 121, and the exit angle of each ray is equal to or smaller than the maximum exit angle α. By such a configuration of the optical system 23, the following effects can be obtained.

First, since the plano-convex lens 231 having the positive power is used, the rays emitted from the measurement region 121 which is much larger than the area of the photosensitive portions 221 to 224 can be focused on the photosensitive portions 221 to 224. Thus, levels of the output signals from the photosensitive portions 221 to 224 is increased. As a result, the accuracy and the repeatability of the measurement can be increased.

Second, when the exit angle of the ray emitted from the LCD panel 12 becomes larger than the maximum exit angle α, the chromaticity and the luminance of the image are largely varied, as mentioned in the description of the prior art. Especially, the larger the exit angle of the rays becomes, the lower the luminance of the image becomes. If the above-mentioned optical system 23 of the embodiment is not used, the photosensitive portions 221 to 224 of the photosensor 22 receive the rays having the exit angle larger than the maximum exit angle α. The chromaticity and the luminance of the image displayed on the measurement region 121 and obtained from the output signals of the photosensitive portions 221 to 224 will include error components due to the rays having the exit angle larger than the maximum exit angle α. However, the exit angle of the rays reach to the photosensitive portions 221 to 224 of the photosensor 22 is restricted to be equal to or smaller than the maximum exit angle α by the optical system 23 in this embodiment, so that error components due to rays having the exit angle larger than the maximum exit angle α are hardly included in the output signal from the photosensitive portions 221 to 224. As a result, the accuracy and the repeatability of the measurement can be increased.

In the above-mentioned description, it is assumed that the lens 231 has no aberration at all or the aberration of the lens 231 is very small. In case that the aberration of the lens 231 is relatively large, it is possible to confirm a position to which the lens 231 is positioned by ray tracing in a manner so that the trails of the rays emitted from the measurement region 121 be substantially the same as the trails in the embodiment, that is, the ray emitted in the normal direction ZZ from the upper end 121a of the measurement region 121 crosses the ray emitted with the maximum exit angle a from the lower end 121b of the measurement region 121 at the top end 221a of the first photosensitive portion 221.

In this embodiment, the opening 212a of the flange 212 of the housing 21 serves as an aperture stop of the optical syster 23 for restricting the field of the measurement region 121, but it is not the indispensable element. For restricting the maximum exit angle α of the rays reaching to the photosensitive portions 221 to 224, it is preferable to provide an aperture stop (or restricting member) in the vicinity of the measurement region 121.

Furthermore, the optical system 23 is configured for including the single plano-convex lens 231 in the embodiment. The optical system 23 is not restricted by configuration of the embodiment. It is possible to configure the optical system 23 including a combination of a plurality of lenses for having positive power.

Modifications of the optical system 23 will be described with reference to figures.

Figure 10:
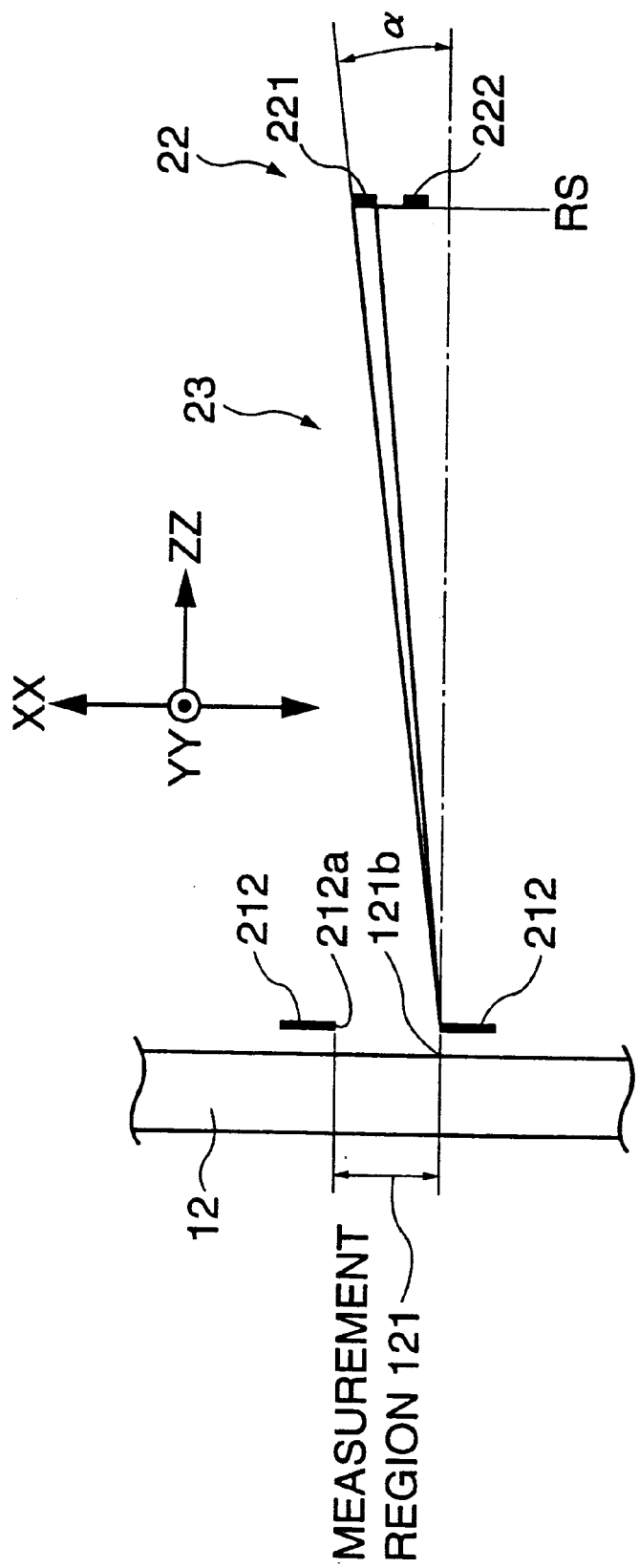
FIG. 10 is an optical path chart showing a first modification of the optical system.

A first modification of the optical system 23 is shown in FIG. 10. In the first modification, any lens is used in the optical system 23. The distance between the opening 212a of the flange 212 and the photosensing plane RS of the photosensor 22 or the diameter of the opening 212a of the flange 212 is adjusted so that the ray emitted from, for example, the lower end 121b of the measurement region 121 with the maximum exit angle α reaches to the end of the photosensing plane RS of the photosensor 22.

Figure 11:
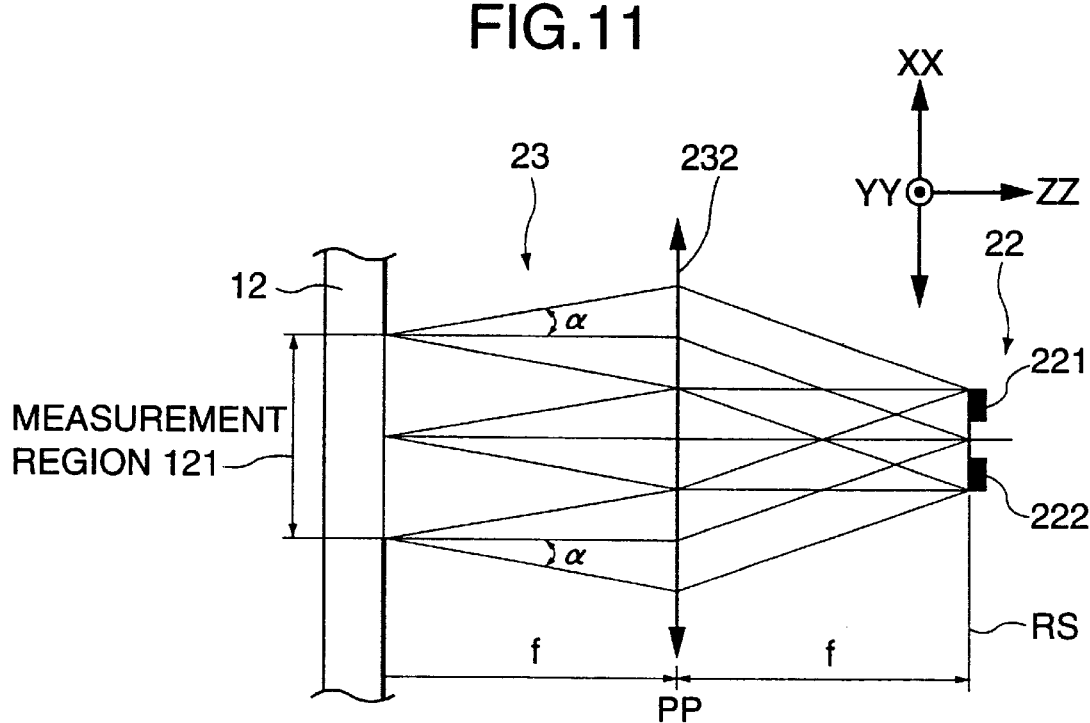
FIG. 11 is an optical path chart showing a second modification of the optical system.
Figure 12:
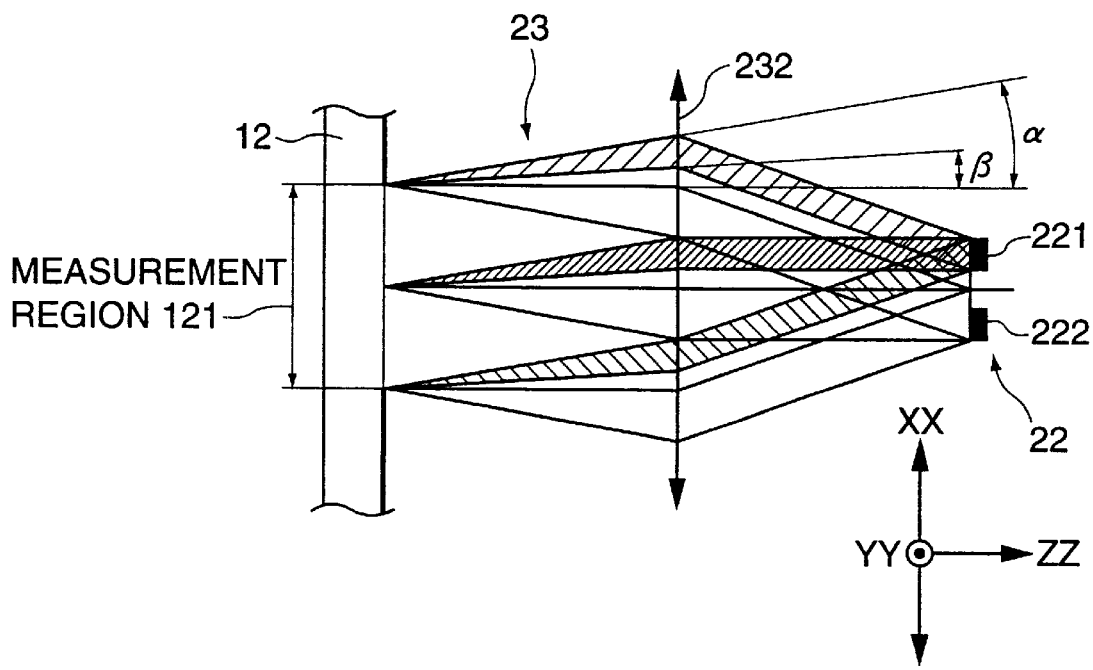
FIG. 12 is an optical path chart for explaining a principle for restricting exit angle of rays by the optical system shown in FIG. 11.

A second modification of the optical system 23 is shown in FIGS. 11 and 12. In the second modification shown in FIG. 11, a lens 232 having a focal length "f" is provided in a manner so that a principal point PP of the lens 232 in the object side is positioned at a position distant by a distance "f" from the measurement region 121, and the photosensing plane RS of the photosensor 22 is positioned at a position distant by a distance "f" from a principal point of the lens 232 in the image side. This configuration is generally called telecentric optical system in which the photosensor 22 serves as an aperture stop of the optical system 23.

As shown in FIG. 12, only the rays emitted from the measurement region 121 and having the exit angle equal to or larger than a predetermined angle β and equal to or smaller than the maximum exit angle α reach to the photosensitive portion 221 to 224 of the photosensor 22. The exit angles α and β depend on the focal length "f" of the lens 232 and the configuration of the photosensor 22. By selecting these elements, the exit angles of the rays reaching to the photosensitive portions 221 to 224 can be made equal to or smaller than the maximum exit angle α.

Figure 13:
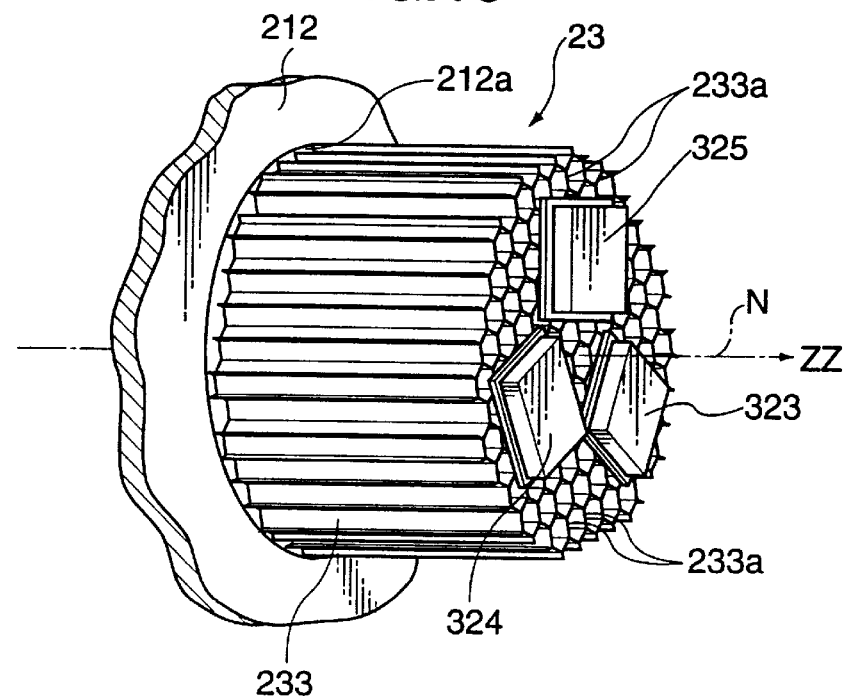
FIG. 13 is a perspective view showing a configuration of a third modification of the optical system.

A third modification of the optical system 23 is shown in FIG. 13. The third modification uses a honeycomb light guide 233 having a plurality of hexagonal tubes 233a. Axes of the tubes 233a are substantially parallel to the normal "N" of the measurement region 121. Numerical aperture of each tube 233a is decided corresponding to the maximum exit angle α. The rays emitted from the LCD panel 12 and entering into the tube 233a from an opening of the tube 233a in the object side pass through the tube 233a and exit from an opening of the tube 233a in the image side. The rays having the exit angle larger than the maximum exit angle α are shielded or absorbed by side walls of the tube 233a. Thus, only the rays having the exit angle equal to or smaller than the maximum exit angle α can exit from the tubes 233a of the honeycomb light guide 233.

Three photosensors 323, 324 and 325 are provided on an end face of the light guide 233 in the image side in a manner so that the photosensors 323 to 325 are respectively disposed on the same circle at intervals of the same pitch (120 degrees) around the center axis ZZ. The photosensor 323 has the spectral sensitivity of $\bar{x}(\lambda)$ having has the highest sensitivity in a region of wavelength of red. The photosensor 324 has the spectral sensitivity of $\bar{y}(\lambda)$ having has the highest sensitivity in a region of wavelength of green. The photosensor 325 has the spectral sensitivity of the spectral sensitivity $\bar{z}(\lambda)$. Thus, output signals corresponding to the tristimulus values X, Y and Z of the image displayed on the measurement region 121 are outputted from the photosensors 323 to 325. The output signals are obtained from the rays passing through the honeycomb light guide 233

Figure 14:
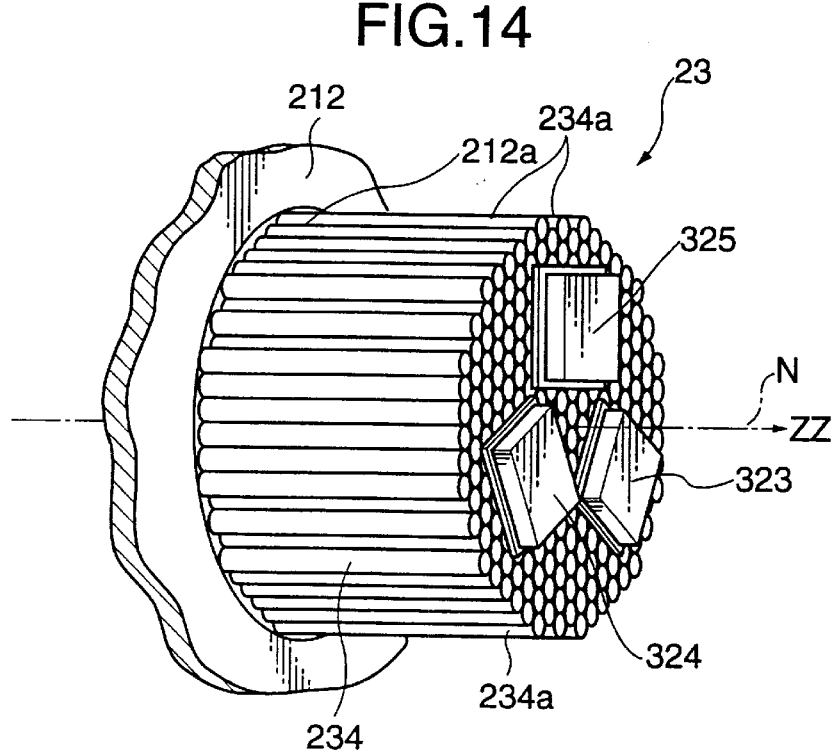
FIG. 14 is a perspective view showing a configuration of a fourth modification.

A fourth modification of the optical system 23 is shown in FIG. 14. In the fourth modification, an optical fiber array 234 in which a plurality of optical fibers 234a are bound is used for guiding the rays emitted from the measurement region 121 to the photosensors 323 to 325. The photosensors 323 to 325 are disposed substantially the same as those in the above-mentioned third modification. Numerical aperture of each optical fiber 234a is decided corresponding to the maximum exit angle α. The rays emitted from the LCD panel 12 and entering into each optical fiber 234a from an opening thereof in the object side move in the optical fiber 234a by repeating of reflection and exit from an opening in the image side. Thus, only the rays having the exit angle equal to or smaller than the maximum exit angle α can exit from the optical fibers 234a of the optical fiber array 234.

Figure 15:
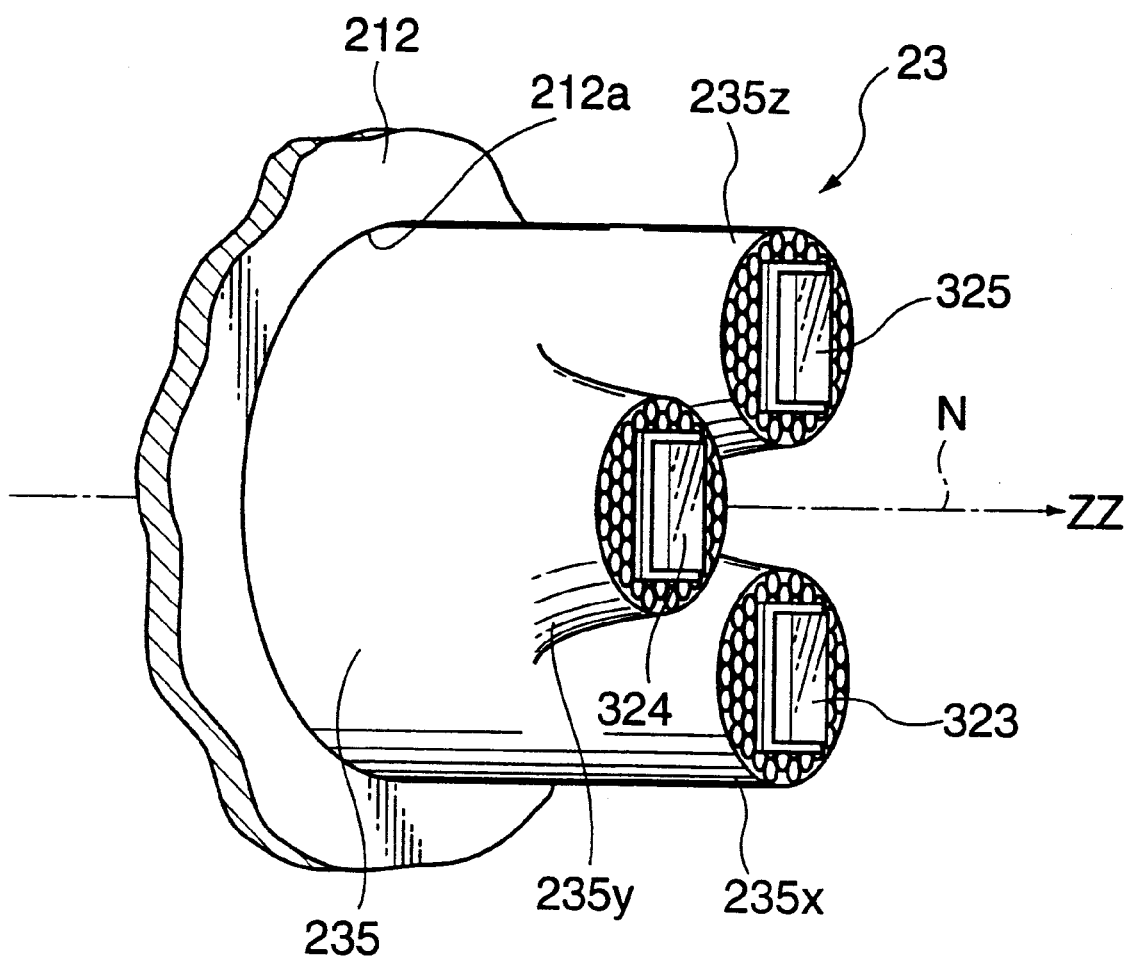
FIG. 15 is a perspective view showing a configuration of a fifth modification of the optical system.

A fifth modification of the optical system 23 is shown in FIG. 15. In the fifth modification, an optical fiber array 235 in which a plurality of flexible optical fibers are bound is used for guiding the rays emitted from the measurement region 121 to the photosensors 323 to 325. An end of the optical fiber array 235 in the image side is separated into three portions 235x, 235y and 235z. The photosensors 323, 324 and 325 are respectively disposed to face the ends of the portions 235x, 235y and 235z of the optical fiber array 235.

Figure 16:
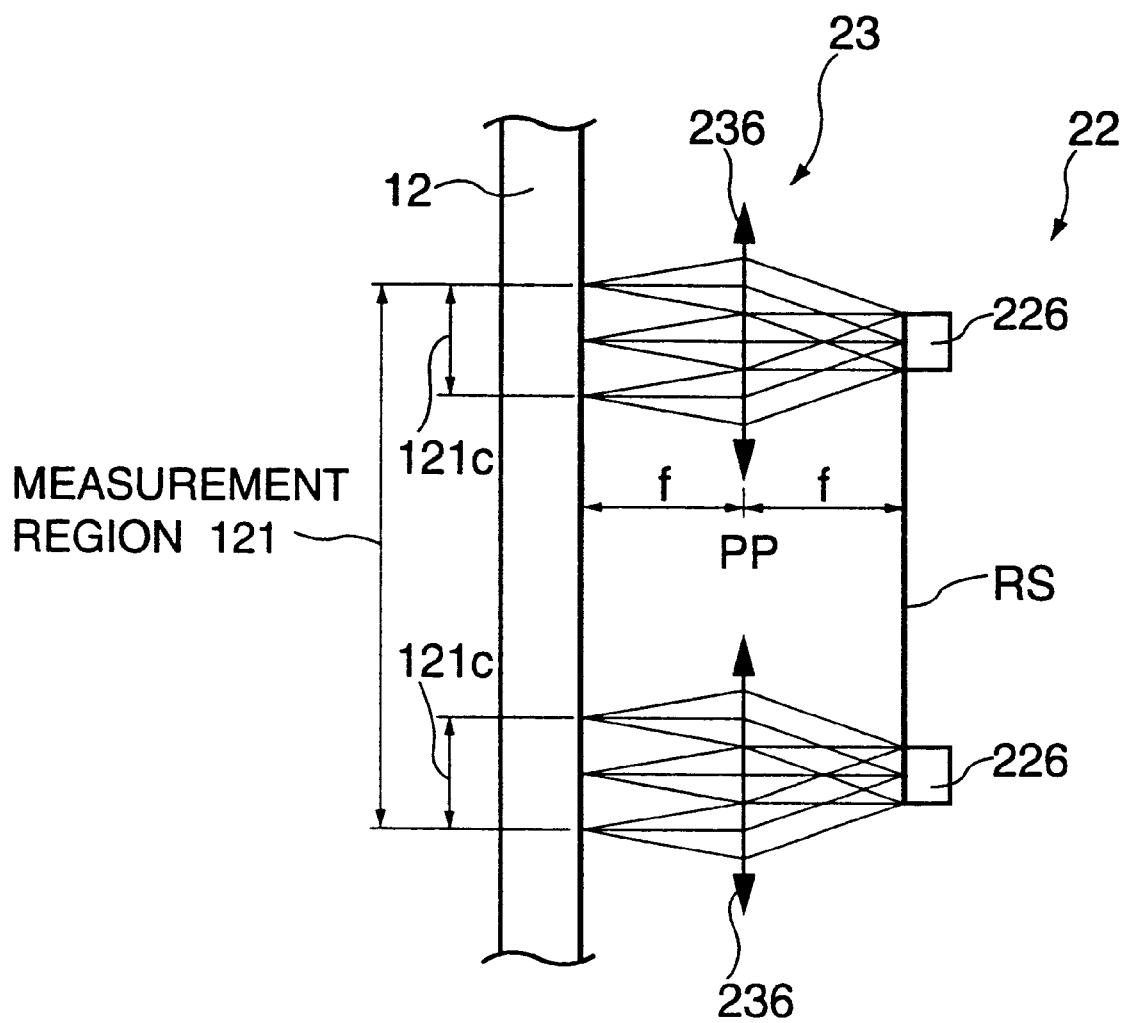
FIG. 16 is an optical path chart showing a configuration of a sixth modification of the optical system.

A sixth modification of the optical system 23 is shown in FIG. 16. In the sixth modification, the optical system 23 comprises a plurality of lenses 236 having a focal length "f" and corresponding to photosensitive portions 226 of the photosensor 22. Each lens 236 is provided in a manner so that the principal point PP of the lens 236 in the object side is positioned distant by a distance "f" from the measurement region 121 and the photosensing plane RS of the photosensor 22 is positioned distant by a distance "f" from a principal plane PP of the lens 236 in the image side. This configuration is also a telecentric optical system. The photosensor 22 serves as an aperture stop of the optical system 23.

By such a configuration, only the rays emitted from a portion 121c corresponding to the lens 236 reach to the photosensitive portion 226 of the photosensor 22. By selecting the focal length "f" of the lenses 236 and the configuration of the photosensor 22, the exit angle of the rays reaching to the photosensitive portion 226 can be made equal to or smaller than the maximum exit angle α.

Figure 17:
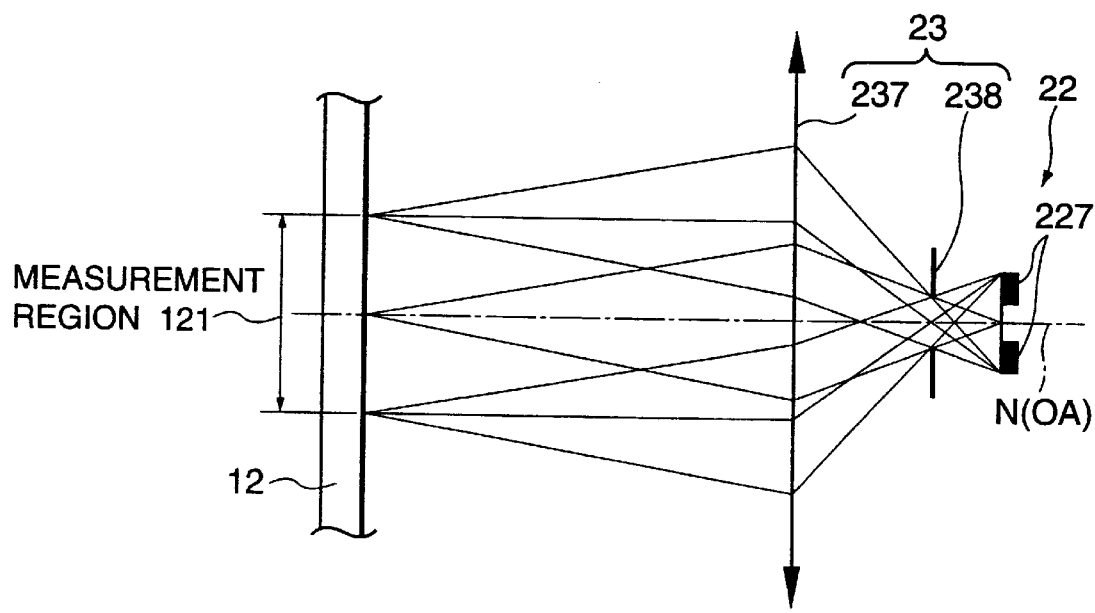
FIG. 17 is an optical path chart showing a configuration of a seventh modification of the optical system.
Figure 18:
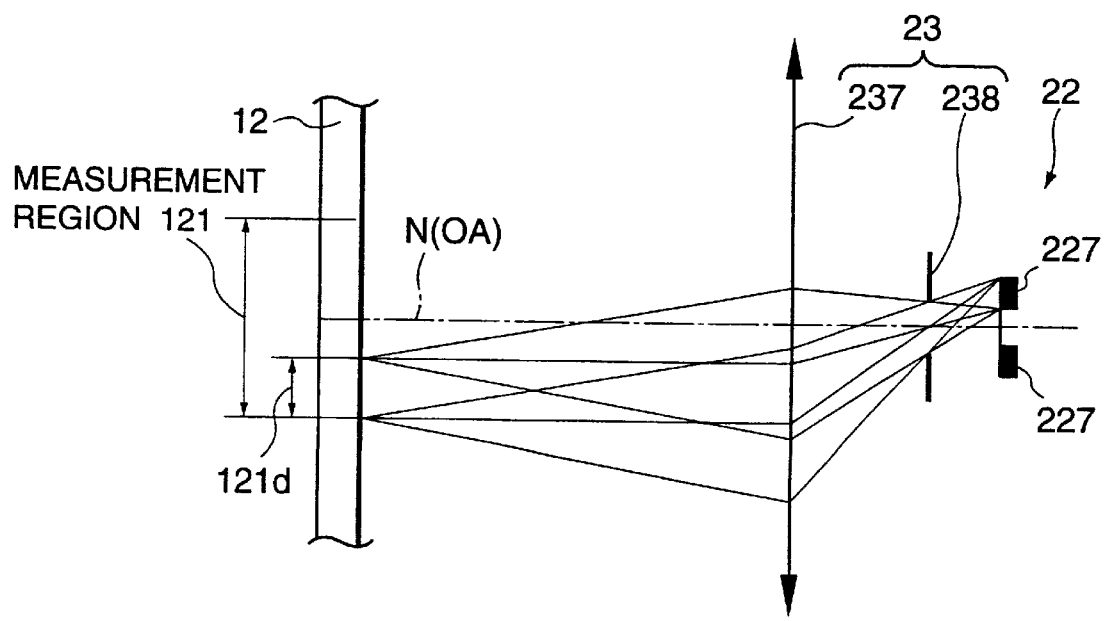
FIG. 18 is an optical path chart for explaining a principle for restricting exit angle of rays by the optical system shown in FIG. 17.

A seventh modification of the optical system 23 is shown in FIGS. 17 and 18. In the seventh modification shown in FIG. 17, the optical system 23 comprises a lens 237 having a focal length "f" and an aperture stop 238. The lens 237 is provided in a manner so that the principal point PP of the lens 237 in the object side is positioned distant by a distance "f" from the measurement region 121 for forming a telecentric optical system. The aperture stop 238 is positioned between the lens 237 and the photosensor 22 so that the measurement region 121 and the photosensing plane RS of the photosensor 22 is optically conjugative.

As shown in FIG. 18, the rays emitted from a portion 121d of the measurement region 121 reach to the photosensitive portion 227 of the photosensor 22 through the lens 237 and the aperture stop 238. By adjusting a diameter of the aperture stop 238, an area of the portion 121d corresponding to the photosensitive portion 227 can be controlled and the exit angle of the rays reaching to the photosensitive portion 227 can be restricted to be equal to or smaller than the maximum exit angle α.

In the modifications shown in FIGS. 11 and 17, the single lens 232 and 237 are used in the optical system 23. It is possible to configure the lens 232 or 237 by combination of a plurality of lenses for having positive power. Similarly, in the modification shown in FIG. 16, a plurality of the single lenses 236 are used in the optical system 23. However, it is possible to configure each lens 236 by combination of a plurality of lenses for having positive power.

Furthermore, in the above-mentioned embodiment, the optical measuring apparatus 2 is used for measuring the optical characteristics of the LCD panel 12. However, the object of the measurement by the optical measuring apparatus 2 is not restricted by the LCD panel 12. It is possible to us e the optical measuring apparatus 2 for any apparatus in which the exit angle of the rays used for the measurement is necessary to restrict equal to or smaller than a predetermined exit angle.

Although the present invention has been fully described by way of example with reference to the accompanying drawings, it is to be understood that various changes and modifications will be apparent to those skilled in the art. Therefore, unless otherwise such changes and modifications depart from the scope of the present invention, they should be construed as being included therein.

What is claimed is:

1. An optical measuring apparatus for measuring an optical characteristic by receiving rays emitted from a region to be measured on a surface of the liquid crystal display panel comprising:
   a housing with a contact portion for contacting on the surface of the liquid crystal display panel at position distant from the region to be measured; and
   a photosensing unit provided on the housing and for receiving rays emitted from the region to be measured when the contact portion contacts the surface of the liquid crystal display panel.

2. The optical measuring apparatus in accordance with claim 1, wherein the housing has light absorptivity and the photosensing unit is disposed inside the housing.

3. The optical measuring apparatus in accordance with claim 2, wherein the housing has a flange portion with an opening through which the rays emitted from the region to be measured enters, and rays emitted from another region except the region to be measured are shielded by the flange portion.

4. The optical measuring apparatus in accordance with claim 1, wherein the contact portion encloses at least a part of the region to be measured.

5. The optical measuring apparatus in accordance with claim 1 further comprising a fixing member for fixing the housing on the liquid crystal display panel.

6. The optical measuring apparatus in accordance with claim 5, wherein the fixing member is a hook by which the housing is hanged on an upper face of a housing of the liquid crystal display panel.

7. The optical measuring apparatus in accordance with claim 1, wherein the photosensing unit has a first photosensing device and a second photosensing device respectively disposed at positions on a photosensing plane distant by a predetermined distance from the surface of the liquid crystal display panel, and symmetrical with respect to a normal line at the center of the region to be measured in a direction where the light distribution of the liquid crystal display panel varies.

8. The optical measuring apparatus in accordance with claim 7, wherein the first photosensing device and the second photosensing device have substantially the same spectral sensitivity.

9. The optical measuring apparatus in accordance with claim 7, wherein the photosensing unit further has a third photosensing device having a spectral sensitivity different from that of the first and second photosensing devices and disposed on an assumed line passing a crossing point of the normal line and the photosensing plane and crossing the direction where the light distribution of the liquid crystal display panel varies substantially at right angle.

10. The optical measuring apparatus in accordance with claim 1 further comprising an optical system for guiding rays emitted from the region to be measured on the surface of the liquid crystal display panel and having exit angle equal to or smaller than a predetermined angle to the photosensing unit.

11. An optical measuring apparatus for measuring an optical characteristic by receiving rays emitted from a region to be measured on a surface of the liquid crystal display panel comprising a first photosensing device and a second photosensing device respectively having substantially the same spectral sensitivity; wherein the first photosensing device and the second photosensing device are disposed at positions on a photosensing plane distant by a predetermined distance from the surface of the liquid crystal display panel, and symmetrical with respect to a normal line at the center of the region to be measured in a direction where the light distribution of the liquid crystal display panel varies.

12. The optical measuring apparatus in accordance with claim 11 further comprising a processor for calculating a measurement value based on outputs obtained from the first and second photosensing devices.

13. The optical measuring apparatus in accordance with claim 12 further comprising a third photosensing device having a spectral sensitivity different from that of the first and second photosensing devices and disposed on an assumed line passing a crossing point of the normal line and the photosensing plane and crossing the direction where the light distribution of the liquid crystal display panel varies substantially at right angle.

14. The optical measuring apparatus in accordance with claim 13, wherein the processor calculates the measurement value by using an added value or a mean value of the outputs of the first and second photosensing devices and an output of the third photosensing device.

15. The optical measuring apparatus in accordance with claim 12 further comprising an interface for transmitting the calculated measurement value to an external apparatus.

16. An optical measuring system consisting of an optical measuring apparatus for measuring an optical characteristic by receiving rays emitted from a region of an object to be measured and a computer which can communicate data between the optical measuring apparatus, wherein the optical measuring apparatus comprises:
a housing with a contact portion for contacting on the surface of the liquid crystal display panel at position distant from the region to be measured;
a photosensing unit provided on the housing and for receiving rays emitted from the region to be measured when the contact portion;
a processor for calculating a measurement value based on outputs obtained from the photosensing unit; and
a transmitter for transmitting the calculated measurement value to the computer; and the computer comprising a receiver for receiving the measurement value transmitted from the transmitter.

17. The optical measuring system in accordance with claim 16, wherein the object to be measured is a liquid crystal display panel.

18. The optical measuring system in accordance with claim 16, wherein the optical measuring apparatus further comprises a fixing member for fixing the housing on the object.

19. The optical measuring system in accordance with claim 16, wherein the photosensing unit has a first photosensing device and a second photosensing device respectively disposed at positions on a photosensing plane distant by a predetermined distance from the surface of the liquid crystal display panel, and symmetrical with respect to a normal line at the center of the region to be measured in a direction where the light distribution of the liquid crystal display panel varies.

20. The optical measuring system in accordance with claim 16, wherein the optical measuring apparatus further comprising an optical system for guiding rays emitted from the region of the object to be measured and having an exit angle equal to or smaller than a predetermined angle to the photosensing unit.

\* \* \* \* \*